United States Patent
Schechter et al.

(10) Patent No.: US 7,799,026 B2
(45) Date of Patent: Sep. 21, 2010

(54) COMPRESSIBLE JAW CONFIGURATION WITH BIPOLAR RF OUTPUT ELECTRODES FOR SOFT TISSUE FUSION

(75) Inventors: David A. Schechter, Longmont, CO (US); Kristin D. Johnson, Louisville, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 10/712,486

(22) Filed: Nov. 13, 2003

(65) Prior Publication Data

US 2004/0143263 A1  Jul. 22, 2004

Related U.S. Application Data

(60) Provisional application No. 60/426,155, filed on Nov. 14, 2002.

(51) Int. Cl.
*A61B 18/14* (2006.01)
(52) U.S. Cl. ............................................ 606/51; 606/49
(58) Field of Classification Search .............. 606/48–52
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |

(Continued)

FOREIGN PATENT DOCUMENTS

CA     2104423      2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Michael Peffley (57) ABSTRACT

The present disclosure relates to electrosurgical instruments for use in sealing various tissues. The instrument includes a housing having a shaft attached thereto and an end effector assembly attached to a distal end of the shaft, wherein the end effector assembly includes first and second jaw members attached thereto. The jaw members are movable relative to one another from a first position for approximating tissue to at least one additional position for grasping tissue therebetween. The jaw members have an elastomeric material disposed on an inner facing tissue contacting surface thereof with the elastomeric materials including an electrode disposed therein. The electrodes are offset a distance X relative to one another such that when the jaw members are closed about the tissue and when the electrodes are activated, electrosurgical energy flows through the tissue in a generally coplanar manner relative to the tissue contacting surfaces.

19 Claims, 5 Drawing Sheets

U.S. PATENT DOCUMENTS

| | | |
|---|---|---|
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,128,099 A | 12/1978 | Bauer |
| 4,165,746 A | 8/1979 | Burgin |
| 4,187,420 A | 2/1980 | Piber |
| 4,236,470 A | 12/1980 | Stenson |
| 4,300,564 A | 11/1981 | Furihata |
| 4,311,145 A | 1/1982 | Esty et al. |
| 4,370,980 A | 2/1983 | Lottick |
| 4,416,276 A | 11/1983 | Newton et al. |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,829,313 A | 5/1989 | Taggart |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A * | 9/1992 | Kamiyama et al. ............ 606/51 |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,318,589 A | 6/1994 | Lichtman |
| 5,324,289 A | 6/1994 | Eggers |
| D348,930 S | 7/1994 | Olson |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |

| | | | | | |
|---|---|---|---|---|---|
| 5,415,657 A | 5/1995 | Taymor-Luria | 5,626,578 A | 5/1997 | Tihon |
| 5,423,810 A | 6/1995 | Goble et al. | 5,626,609 A | 5/1997 | Zvenyatsky et al. |
| 5,425,739 A | 6/1995 | Jessen | 5,630,833 A | 5/1997 | Katsaros et al. |
| 5,429,616 A | 7/1995 | Schaffer | 5,637,110 A | 6/1997 | Pennybacker et al. |
| 5,431,674 A | 7/1995 | Basile et al. | 5,643,294 A | 7/1997 | Tovey et al. |
| 5,438,302 A | 8/1995 | Goble | 5,647,869 A | 7/1997 | Goble et al. |
| 5,439,478 A | 8/1995 | Palmer | 5,647,871 A | 7/1997 | Levine et al. |
| 5,441,517 A | 8/1995 | Kensey et al. | 5,649,959 A | 7/1997 | Hannam et al. |
| 5,443,463 A * | 8/1995 | Stern et al. .................... 606/51 | 5,655,650 A | 8/1997 | Naitou |
| 5,443,464 A | 8/1995 | Russell et al. | 5,658,281 A | 8/1997 | Heard |
| 5,443,480 A | 8/1995 | Jacobs et al. | D384,413 S | 9/1997 | Zlock et al. |
| 5,445,638 A | 8/1995 | Rydell et al. | 5,662,667 A | 9/1997 | Knodel |
| 5,445,658 A | 8/1995 | Durrfeld et al. | 5,665,100 A | 9/1997 | Yoon |
| 5,449,480 A | 9/1995 | Kuriya et al. | 5,667,526 A | 9/1997 | Levin |
| 5,451,224 A | 9/1995 | Goble et al. | 5,674,220 A | 10/1997 | Fox et al. |
| 5,454,823 A | 10/1995 | Richardson et al. | 5,674,229 A | 10/1997 | Tovey et al. |
| 5,454,827 A | 10/1995 | Aust et al. | 5,681,282 A | 10/1997 | Eggers et al. |
| 5,456,684 A * | 10/1995 | Schmidt et al. .................... 606/41 | 5,688,270 A * | 11/1997 | Yates et al. .................... 606/51 |
| 5,458,598 A | 10/1995 | Feinberg et al. | 5,690,652 A | 11/1997 | Wurster et al. |
| 5,460,629 A | 10/1995 | Shlain et al. | 5,690,653 A | 11/1997 | Richardson et al. |
| 5,461,765 A | 10/1995 | Linden et al. | 5,693,051 A | 12/1997 | Schulze et al. |
| 5,462,546 A | 10/1995 | Rydell | 5,693,920 A | 12/1997 | Maeda |
| 5,472,442 A | 12/1995 | Klicek | 5,695,522 A | 12/1997 | LeMaire, III et al. |
| 5,472,443 A | 12/1995 | Cordis et al. | 5,700,261 A | 12/1997 | Brinkerhoff |
| 5,478,351 A | 12/1995 | Meade et al. | 5,700,270 A | 12/1997 | Peyser et al. |
| 5,480,406 A | 1/1996 | Nolan et al. | 5,702,390 A | 12/1997 | Austin et al. |
| 5,480,409 A | 1/1996 | Riza | 5,707,369 A | 1/1998 | Vaitekunas et al. |
| 5,484,436 A * | 1/1996 | Eggers et al. .................... 606/48 | 5,709,680 A | 1/1998 | Yates et al. |
| 5,496,312 A * | 3/1996 | Klicek .................... 606/34 | 5,716,366 A | 2/1998 | Yates |
| 5,496,317 A | 3/1996 | Goble et al. | 5,727,428 A | 3/1998 | LeMaire, III et al. |
| 5,496,347 A | 3/1996 | Hashiguchi et al. | 5,735,848 A | 4/1998 | Yates et al. |
| 5,499,997 A | 3/1996 | Sharpe et al. | 5,743,906 A | 4/1998 | Parins et al. |
| 5,509,922 A | 4/1996 | Aranyi et al. | 5,752,973 A | 5/1998 | Kieturakis |
| 5,514,134 A | 5/1996 | Rydell et al. | 5,755,717 A | 5/1998 | Yates et al. |
| 5,527,313 A | 6/1996 | Scott et al. | 5,759,188 A | 6/1998 | Yoon |
| 5,528,833 A | 6/1996 | Sakuma | 5,766,130 A | 6/1998 | Selmonosky |
| 5,529,067 A | 6/1996 | Larsen et al. | 5,766,166 A | 6/1998 | Hooven |
| 5,531,744 A | 7/1996 | Nardella et al. | 5,766,170 A | 6/1998 | Eggers |
| 5,536,251 A | 7/1996 | Evard et al. | 5,766,196 A | 6/1998 | Griffiths |
| 5,540,684 A | 7/1996 | Hassler, Jr. | 5,769,849 A | 6/1998 | Eggers |
| 5,540,685 A | 7/1996 | Parins et al. | 5,772,655 A | 6/1998 | Bauer et al. |
| 5,540,706 A | 7/1996 | Aust et al. | 5,772,670 A | 6/1998 | Brosa |
| 5,540,715 A | 7/1996 | Katsaros et al. | 5,776,128 A | 7/1998 | Eggers |
| 5,542,945 A | 8/1996 | Fritzsch | 5,776,130 A | 7/1998 | Buysse et al. |
| 5,558,672 A | 9/1996 | Edwards et al. | 5,779,646 A | 7/1998 | Koblish et al. |
| 5,562,619 A | 10/1996 | Mirarchi et al. | 5,779,701 A | 7/1998 | McBrayer et al. |
| 5,562,699 A | 10/1996 | Heimberger et al. | 5,792,137 A | 8/1998 | Carr et al. |
| 5,562,720 A | 10/1996 | Stern et al. | 5,792,165 A | 8/1998 | Klieman et al. |
| 5,564,615 A | 10/1996 | Bishop et al. | 5,792,177 A | 8/1998 | Kaseda |
| 5,569,241 A | 10/1996 | Edwards | 5,797,537 A | 8/1998 | Oberlin et al. |
| 5,569,243 A | 10/1996 | Kortenbach et al. | 5,797,938 A | 8/1998 | Paraschac et al. |
| 5,571,100 A | 11/1996 | Goble et al. | 5,797,958 A | 8/1998 | Yoon |
| 5,573,424 A | 11/1996 | Poppe | 5,800,449 A | 9/1998 | Wales |
| 5,573,534 A | 11/1996 | Stone | 5,807,393 A | 9/1998 | Williamson, IV et al. |
| 5,573,535 A | 11/1996 | Viklund | 5,810,764 A | 9/1998 | Eggers et al. |
| 5,575,799 A | 11/1996 | Bolanos et al. | 5,810,805 A | 9/1998 | Sutcu et al. |
| 5,579,781 A | 12/1996 | Cooke | 5,810,808 A | 9/1998 | Eggers |
| 5,582,611 A | 12/1996 | Tsukagoshi et al. | 5,810,811 A * | 9/1998 | Yates et al. .................... 606/50 |
| 5,582,617 A | 12/1996 | Klieman et al. | 5,810,877 A | 9/1998 | Roth et al. |
| 5,585,896 A | 12/1996 | Yamazaki et al. | 5,814,043 A | 9/1998 | Shapeton |
| 5,590,570 A | 1/1997 | LeMaire, III et al. | 5,814,054 A | 9/1998 | Kortenbach et al. |
| 5,591,181 A | 1/1997 | Stone et al. | 5,817,119 A | 10/1998 | Klieman et al. |
| 5,597,107 A | 1/1997 | Knodel et al. | 5,820,630 A | 10/1998 | Lind |
| 5,601,224 A | 2/1997 | Bishop et al. | 5,824,978 A | 10/1998 | Karasik et al. |
| 5,601,601 A | 2/1997 | Tal et al. | 5,827,271 A | 10/1998 | Buysse et al. |
| 5,601,641 A | 2/1997 | Stephens | 5,827,279 A | 10/1998 | Hughett et al. |
| 5,603,711 A | 2/1997 | Parins et al. | 5,827,281 A | 10/1998 | Levin |
| 5,603,723 A | 2/1997 | Aranyi et al. | 5,833,690 A | 11/1998 | Yates et al. |
| 5,611,798 A | 3/1997 | Eggers | 5,843,080 A | 12/1998 | Fleenor et al. |
| 5,611,808 A | 3/1997 | Hossain et al. | 5,849,022 A | 12/1998 | Sakashita et al. |
| 5,611,813 A | 3/1997 | Lichtman | 5,853,412 A | 12/1998 | Mayenberger |
| 5,620,415 A | 4/1997 | Lucey et al. | 5,859,527 A | 1/1999 | Cook |
| 5,620,459 A | 4/1997 | Lichtman | 5,860,976 A | 1/1999 | Billings et al. |

| | | | | | | |
|---|---|---|---|---|---|---|
| 5,876,401 A | 3/1999 | Schulze et al. | | H1904 H | 10/2000 | Yates et al. |
| 5,876,412 A | 3/1999 | Piraka | | 6,126,658 A | 10/2000 | Baker |
| 5,891,141 A | 4/1999 | Rydell | | 6,126,665 A | 10/2000 | Yoon |
| 5,891,142 A | 4/1999 | Eggers et al. | | 6,139,563 A | 10/2000 | Cosgrove, III et al. |
| 5,893,863 A | 4/1999 | Yoon | | 6,143,005 A | 11/2000 | Yoon et al. |
| 5,893,875 A | 4/1999 | O'Connor et al. | | 6,152,923 A | 11/2000 | Ryan |
| 5,893,877 A | 4/1999 | Gampp, Jr. et al. | | 6,162,220 A | 12/2000 | Nezhat |
| 5,897,563 A | 4/1999 | Yoon et al. | | 6,171,316 B1 | 1/2001 | Kovac et al. |
| 5,902,301 A | 5/1999 | Olig | | 6,174,309 B1 | 1/2001 | Wrublewski et al. |
| 5,906,630 A | 5/1999 | Anderhub et al. | | 6,178,628 B1 | 1/2001 | Clemens et al. |
| 5,908,420 A | 6/1999 | Parins et al. | | 6,179,834 B1 | 1/2001 | Buysse et al. |
| 5,911,719 A | 6/1999 | Eggers | | 6,179,837 B1 | 1/2001 | Hooven |
| 5,913,874 A | 6/1999 | Berns et al. | | 6,183,467 B1 | 2/2001 | Shapeton et al. |
| 5,921,916 A | 7/1999 | Aeikens et al. | | 6,187,003 B1 | 2/2001 | Buysse et al. |
| 5,921,984 A | 7/1999 | Sutcu et al. | | 6,190,386 B1 | 2/2001 | Rydell |
| 5,925,043 A | 7/1999 | Kumar et al. | | 6,190,400 B1 | 2/2001 | Vandemoer et al. |
| 5,928,136 A | 7/1999 | Barry | | 6,193,718 B1 | 2/2001 | Kortenbach et al. |
| 5,935,126 A | 8/1999 | Riza | | 6,206,876 B1 | 3/2001 | Levine et al. |
| 5,941,869 A | 8/1999 | Patterson et al. | | 6,206,877 B1 | 3/2001 | Kese et al. |
| 5,944,718 A | 8/1999 | Dafforn et al. | | 6,206,893 B1 | 3/2001 | Klein et al. |
| 5,951,546 A | 9/1999 | Lorentzen | | 6,214,028 B1 | 4/2001 | Yoon et al. |
| 5,951,549 A | 9/1999 | Richardson et al. | | 6,217,602 B1 | 4/2001 | Redmon |
| 5,954,720 A | 9/1999 | Wilson et al. | | 6,217,615 B1 | 4/2001 | Sioshansi et al. |
| 5,954,731 A | 9/1999 | Yoon | | 6,223,100 B1 | 4/2001 | Green |
| 5,954,733 A | 9/1999 | Yoon | | 6,224,593 B1 | 5/2001 | Ryan et al. |
| 5,957,923 A | 9/1999 | Hahnen et al. | | 6,224,614 B1 | 5/2001 | Yoon |
| 5,957,937 A | 9/1999 | Yoon | | 6,228,080 B1 | 5/2001 | Gines |
| 5,961,514 A | 10/1999 | Long et al. | | 6,228,083 B1 | 5/2001 | Lands et al. |
| 5,976,132 A | 11/1999 | Morris | | 6,248,124 B1 | 6/2001 | Pedros et al. |
| 5,984,932 A | 11/1999 | Yoon | | 6,248,944 B1 | 6/2001 | Ito |
| 5,984,938 A | 11/1999 | Yoon | | 6,261,307 B1 | 7/2001 | Yoon et al. |
| 5,984,939 A | 11/1999 | Yoon | | 6,267,761 B1 | 7/2001 | Ryan |
| 5,989,277 A | 11/1999 | LeMaire, III et al. | | 6,270,497 B1 | 8/2001 | Sekino et al. |
| 5,993,466 A | 11/1999 | Yoon | | 6,270,508 B1 | 8/2001 | Klieman et al. |
| 5,993,467 A | 11/1999 | Yoon | | 6,273,887 B1 | 8/2001 | Yamauchi et al. |
| 6,004,332 A | 12/1999 | Yoon et al. | | 6,277,117 B1 | 8/2001 | Tetzlaff et al. |
| 6,004,335 A | 12/1999 | Vaitekunas et al. | | 6,280,458 B1 | 8/2001 | Boche et al. |
| 6,010,516 A | 1/2000 | Hulka et al. | | 6,283,961 B1 | 9/2001 | Underwood et al. |
| 6,017,358 A | 1/2000 | Yoon et al. | | D449,886 S | 10/2001 | Tetzlaff et al. |
| 6,021,693 A | 2/2000 | Feng-Sing | | 6,298,550 B1 | 10/2001 | Kirwan |
| 6,024,741 A | 2/2000 | Willaimson et al. | | 6,319,262 B1 | 11/2001 | Bates et al. |
| 6,024,743 A | 2/2000 | Edwards | | 6,322,561 B1 | 11/2001 | Eggers et al. |
| 6,024,744 A | 2/2000 | Kese et al. | | 6,322,580 B1 | 11/2001 | Kanner |
| 6,027,522 A | 2/2000 | Palmer | | 6,325,795 B1 | 12/2001 | Lindemann et al. |
| 6,030,384 A | 2/2000 | Nezhat | | 6,334,860 B1 | 1/2002 | Dorn |
| 6,033,399 A | 3/2000 | Gines | | 6,334,861 B1 | 1/2002 | Chandler et al. |
| 6,039,733 A | 3/2000 | Buysse et al. | | 6,350,264 B1 | 2/2002 | Hooven |
| 6,041,679 A | 3/2000 | Slater et al. | | 6,352,536 B1 | 3/2002 | Buysse et al. |
| 6,050,996 A | 4/2000 | Schmaltz et al. | | 6,358,259 B1 | 3/2002 | Swain et al. |
| 6,053,914 A | 4/2000 | Eggers et al. | | 6,364,879 B1 | 4/2002 | Chen et al. |
| 6,053,933 A | 4/2000 | Balazs et al. | | D457,958 S | 5/2002 | Dycus et al. |
| D424,694 S | 5/2000 | Tetzlaff et al. | | D457,959 S | 5/2002 | Tetzlaff et al. |
| D425,201 S | 5/2000 | Tetzlaff et al. | | 6,387,094 B1 | 5/2002 | Eitenmuller |
| 6,059,782 A | 5/2000 | Novak et al. | | 6,398,779 B1 | 6/2002 | Buysse et al. |
| 6,066,139 A | 5/2000 | Ryan et al. | | 6,402,747 B1 | 6/2002 | Lindemann et al. |
| 6,077,287 A | 6/2000 | Taylor et al. | | 6,409,728 B1 | 6/2002 | Ehr et al. |
| 6,080,180 A | 6/2000 | Yoon et al. | | H2037 H | 7/2002 | Yates et al. |
| RE36,795 E | 7/2000 | Rydell | | 6,419,675 B1 | 7/2002 | Gallo, Sr. |
| 6,083,223 A | 7/2000 | Baker | | 6,425,896 B1 | 7/2002 | Baltschun et al. |
| 6,086,586 A * | 7/2000 | Hooven .................. 606/50 | | 6,432,112 B2 | 8/2002 | Brock et al. |
| 6,086,601 A | 7/2000 | Yoon | | 6,443,952 B1 | 9/2002 | Mulier et al. |
| 6,090,107 A | 7/2000 | Borgmeier et al. | | 6,443,970 B1 | 9/2002 | Schulze et al. |
| 6,096,031 A | 8/2000 | Mitchell et al. | | 6,451,018 B1 | 9/2002 | Lands et al. |
| 6,096,037 A | 8/2000 | Mulier et al. | | 6,458,128 B1 | 10/2002 | Schulze |
| 6,099,550 A | 8/2000 | Yoon | | 6,458,130 B1 | 10/2002 | Frazier et al. |
| 6,102,909 A | 8/2000 | Chen et al. | | 6,461,352 B2 | 10/2002 | Morgan et al. |
| 6,106,542 A | 8/2000 | Toybin et al. | | 6,461,368 B2 | 10/2002 | Fogarty et al. |
| 6,110,171 A | 8/2000 | Rydell | | 6,464,701 B1 | 10/2002 | Hooven et al. |
| 6,113,596 A | 9/2000 | Hooven et al. | | 6,464,704 B2 | 10/2002 | Schmaltz et al. |
| 6,113,598 A * | 9/2000 | Baker .................... 606/51 | | 6,485,489 B2 | 11/2002 | Teirstein et al. |
| 6,117,158 A | 9/2000 | Measamer et al. | | 6,494,888 B1 | 12/2002 | Laufer et al. |
| 6,122,549 A | 9/2000 | Sharkey et al. | | 6,503,248 B1 | 1/2003 | Levine |
| 6,123,701 A | 9/2000 | Nezhat | | 6,506,189 B1 | 1/2003 | Rittman, III et al. |

| | | |
|---|---|---|
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,251 B1 | 2/2003 | Ni et al. |
| 6,517,539 B1 | 2/2003 | Smith et al. |
| 6,533,784 B2 | 3/2003 | Truckai et al. |
| 6,544,264 B2 | 4/2003 | Levine et al. |
| 6,545,239 B2 | 4/2003 | Spedale et al. |
| 6,569,105 B1 | 5/2003 | Kortenbach et al. |
| 6,569,162 B2 | 5/2003 | He |
| 6,582,450 B2 | 6/2003 | Ouchi |
| 6,605,790 B2 | 8/2003 | Yoshida |
| 6,620,161 B2 | 9/2003 | Schulze et al. |
| 6,620,184 B2 | 9/2003 | De Laforcade et al. |
| 6,638,287 B2 | 10/2003 | Danitz et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 * | 1/2004 | Wampler et al. .............. 606/51 |
| 6,676,676 B2 | 1/2004 | Danitz et al. |
| 6,685,724 B1 | 2/2004 | Haluck |
| 6,693,246 B1 | 2/2004 | Rudolph et al. |
| 6,723,092 B2 | 4/2004 | Brown et al. |
| 6,726,694 B2 | 4/2004 | Blatter et al. |
| 6,733,498 B2 | 5/2004 | Paton et al. |
| 6,743,229 B2 | 6/2004 | Buysse et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| D493,888 S | 8/2004 | Reschke |
| 6,770,072 B1 * | 8/2004 | Truckai et al. ................ 606/52 |
| 6,773,409 B2 * | 8/2004 | Truckai et al. ................ 601/2 |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,776,780 B2 | 8/2004 | Mulier et al. |
| 6,786,905 B2 | 9/2004 | Swanson et al. |
| D496,997 S | 10/2004 | Dycus et al. |
| 6,800,825 B1 | 10/2004 | Sasaki et al. |
| 6,802,843 B2 | 10/2004 | Truckai et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,889,116 B2 | 5/2005 | Jinno |
| 6,914,201 B2 | 7/2005 | Van Vooren et al. |
| 6,926,716 B2 * | 8/2005 | Baker et al. .................... 606/51 |
| 6,929,644 B2 | 8/2005 | Truckai et al. |
| 6,932,810 B2 | 8/2005 | Ryan |
| 6,932,816 B2 * | 8/2005 | Phan ........................... 606/49 |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,964,662 B2 | 11/2005 | Kidooka |
| 6,972,017 B2 | 12/2005 | Smith et al. |
| 6,981,628 B2 | 1/2006 | Wales |
| 6,987,244 B2 | 1/2006 | Bauer |
| 6,997,931 B2 | 2/2006 | Sauer et al. |
| 7,001,381 B2 | 2/2006 | Harano et al. |
| 7,033,354 B2 | 4/2006 | Keppel |
| 7,052,489 B2 | 5/2006 | Griego et al. |
| 7,063,715 B2 | 6/2006 | Onuki et al. |
| 7,083,618 B2 | 8/2006 | Couture et al. |
| 7,083,620 B2 | 8/2006 | Jahns et al. |
| 7,087,051 B2 | 8/2006 | Bourne et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,118,570 B2 | 10/2006 | Tetzlaff et al. |
| 7,118,587 B2 | 10/2006 | Dycus et al. |
| 7,153,314 B2 | 12/2006 | Laufer et al. |
| 7,179,255 B2 | 2/2007 | Lettice et al. |
| 7,223,264 B2 | 5/2007 | Daniel et al. |
| 7,244,257 B2 | 7/2007 | Podjahsky et al. |
| 7,246,734 B2 | 7/2007 | Shelton, IV |
| 7,248,944 B2 | 7/2007 | Green |
| 7,311,709 B2 | 12/2007 | Truckai et al. |
| 7,318,823 B2 | 1/2008 | Sharps et al. |
| 7,338,526 B2 | 3/2008 | Steinberg |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0018331 A1 | 1/2003 | Dycus et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0073238 A1 | 4/2004 | Makower |
| 2004/0073256 A1 | 4/2004 | Marchitto et al. |
| 2004/0116979 A1 | 6/2004 | Truckai et al. |
| 2004/0147925 A1 | 7/2004 | Buysse et al. |
| 2004/0148035 A1 | 7/2004 | Barrett et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |

| | | |
|---|---|---|
| 2004/0230189 A1 | 11/2004 | Keppel |
| 2004/0236325 A1* | 11/2004 | Tetzlaff et al. .......... 606/51 |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149151 A1 | 7/2005 | Orszulak et al. |
| 2005/0154387 A1 | 7/2005 | Moses et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0283093 A1 | 12/2006 | Petrovic et al. |
| 2007/0198011 A1 | 8/2007 | Sugita |
| 2008/0039836 A1 | 2/2008 | Odom et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 3612646 | 4/1987 |
| DE | 8712328 | 3/1988 |
| DE | 4403252 | 8/1995 |
| DE | 19515914 | 7/1996 |
| DE | 29616210 | 1/1997 |
| DE | 19608716 | 4/1997 |
| DE | 19751108 | 5/1999 |
| DE | 19738457 | 1/2009 |
| EP | 0364216 A1 | 4/1990 |
| EP | 0467501 | 1/1992 |
| EP | 0518230 A1 | 12/1992 |
| EP | 0 541 930 B1 | 5/1993 |
| EP | 0572131 | 12/1993 |
| EP | 0584787 A1 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 0853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1330991 A1 | 7/2003 |
| EP | 1486177 A2 | 6/2004 |
| EP | 0774232 | 1/2005 |
| EP | 1532932 A1 | 5/2005 |
| EP | 1642543 | 4/2006 |
| EP | 1649821 | 4/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |

| | | | | | | |
|---|---|---|---|---|---|---|
| GB | 2214430 A | 6/1989 | | WO | WO 2008/045350 | 4/2008 |
| JP | 501068 | 9/1984 | | | | |
| JP | 502328 | 3/1992 | | | | |
| JP | 5-40112 | 2/1993 | | | | |
| JP | 06343644 A2 | 12/1994 | | | | |
| JP | 07265328 A2 | 10/1995 | | | | |
| JP | 08056955 A2 | 3/1996 | | | | |
| JP | 08252263 A2 | 10/1996 | | | | |
| JP | 09010223 A2 | 1/1997 | | | | |
| JP | 11244298 A2 | 9/1999 | | | | |
| JP | 2000342599 A2 | 12/2000 | | | | |
| JP | 2000350732 A2 | 12/2000 | | | | |
| JP | 2001008944 A2 | 1/2001 | | | | |
| JP | 2001029356 A2 | 2/2001 | | | | |
| JP | 2001128990 A2 | 5/2001 | | | | |
| SU | 401367 | 11/1974 | | | | |
| WO | WO 92/06642 | 4/1992 | | | | |
| WO | WO 93/21845 | 11/1993 | | | | |
| WO | WO 94/08524 A | 4/1994 | | | | |
| WO | WO 95/02369 | 1/1995 | | | | |
| WO | WO 95/07662 | 3/1995 | | | | |
| WO | WO 96/22056 | 7/1996 | | | | |
| WO | WO 96/13218 | 9/1996 | | | | |
| WO | WO 97/00646 | 1/1997 | | | | |
| WO | WO 97/00647 | 1/1997 | | | | |
| WO | WO 97/10784 | 3/1997 | | | | |
| WO | WO 97/24073 | 7/1997 | | | | |
| WO | WO 97/24993 | 7/1997 | | | | |
| WO | WO 98/27880 | 7/1998 | | | | |
| WO | WO 99/03407 | 1/1999 | | | | |
| WO | WO 99/03408 | 1/1999 | | | | |
| WO | WO 99/03409 | 1/1999 | | | | |
| WO | WO 99/12488 A | 3/1999 | | | | |
| WO | WO 99/23933 | 5/1999 | | | | |
| WO | WO 99/40857 | 8/1999 | | | | |
| WO | WO 99/40881 | 8/1999 | | | | |
| WO | WO 99/51158 | 10/1999 | | | | |
| WO | WO 99/66850 | 12/1999 | | | | |
| WO | WO 99/66850 A | 12/1999 | | | | |
| WO | WO 00/24330 | 5/2000 | | | | |
| WO | WO 00/24331 | 5/2000 | | | | |
| WO | WO 00/36986 | 6/2000 | | | | |
| WO | WO 00/41638 | 7/2000 | | | | |
| WO | WO 00/53112 | 9/2000 | | | | |
| WO | WO 01/17448 A | 3/2001 | | | | |
| WO | WO 01/54604 | 8/2001 | | | | |
| WO | WO 02/07627 | 1/2002 | | | | |
| WO | WO 02/080783 | 10/2002 | | | | |
| WO | WO 02/080784 | 10/2002 | | | | |
| WO | WO 02/080785 | 10/2002 | | | | |
| WO | WO 02/080786 | 10/2002 | | | | |
| WO | WO 02/080793 | 10/2002 | | | | |
| WO | WO 02/080794 | 10/2002 | | | | |
| WO | WO 02/080795 | 10/2002 | | | | |
| WO | WO 02/080796 | 10/2002 | | | | |
| WO | WO 02/080796 A1 | 10/2002 | | | | |
| WO | WO 02/080797 | 10/2002 | | | | |
| WO | WO 02/080798 | 10/2002 | | | | |
| WO | WO 02/080799 | 10/2002 | | | | |
| WO | WO 02/081170 | 10/2002 | | | | |
| WO | WO 03/061500 | 7/2003 | | | | |
| WO | WO 03/101311 | 12/2003 | | | | |
| WO | WO 2004/032777 | 4/2004 | | | | |
| WO | WO 2004/052221 A1 | 6/2004 | | | | |
| WO | WO 2004/073490 | 9/2004 | | | | |
| WO | WO 2004/082495 | 9/2004 | | | | |
| WO | WO 2004/082495 A1 | 9/2004 | | | | |
| WO | WO 2004/098383 A1 | 11/2004 | | | | |
| WO | WO 2004/103156 | 12/2004 | | | | |
| WO | WO 2008/045348 | 4/2008 | | | | |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine. St Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature.

LigaSure Vessel Sealing System, the Seal of Confidence in General, Gynecologic, Urologic, and Laparaoscopic Surgery Sales/Product Literature.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With the LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" Sales/Product Literature.

Jarrett et al., "Use of the LigaSure Vessel Sealing System for Peri-Hilar Vessels in Laparoscopic Nephrectomy" Sales/Product Literature.

E. David Crawford "Evaluation of a New Vessel Sealing Device in Urologic Cancer Surgey" Sales/Product Literature.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, Vol. 6, No. 1, 2002.

Dulemba et al. "Use of a Bipolar Electrothermal Vessel Sealer in Laparoscopically Assisted Vaginal Hysterectomy" Sales/Product Literature.

Johnson et al. "Evaluation of a Bipolar electrothermal Vessel Sealing Device in Hemorrhoidectomy" Sales/Product Literature.

Int'l Search Report PCT/US01/11218.
Int'l Search Report PCT/US99/24869.
Int'l Search Report PCT/US98/18640.
Int'l Search Report PCT/US98/23950.
PCT/US01/11340, International Search Report.
PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.

"Innovations in Electrosurgery" Sales/Product Literature; Dec. 31, 2000.

LigaSure Vessel Sealing System, the Seal of Confidence in General, Gynecologic, Urologic, and Laparoscopic Surgery Sales/Product Literature; Jan. 2004.

Olsson et al. "Radical Cystectomy in Females" Current Surgical Techniques in Urology, vol. 14, Issue 3, 2001.

Dulemba et al. "Use of a Bipolar Electrothermal Vessel Sealer in Laparoscopically Assisted Vaginal Hysterectomy" Sales Product Literature; Jan. 2004.

Johnson et al. "Evaluation of a Bipolar electrothennal Vessel Sealing Device in Hemorrhoidectomy" Sales Product Literature; Jan. 2004.

International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Crouch et al. "A Velocity-Dependent Model for Needle Insertion in Soft Tissue" MICCAI 2005; LNCS 3750 pp. 624-632, Dated: 2005.

Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
US 6,090,109, 07/2000, Lands et al. (withdrawn)
US 6,663,629, 12/2003, Buysse et al. (withdrawn)

* cited by examiner

COMPRESSIBLE JAW CONFIGURATION WITH BIPOLAR RF OUTPUT ELECTRODES FOR SOFT TISSUE FUSION

CROSS REFERENCE TO RELATED APPLICATIONS

This application claims the benefit of U.S. Provisional Application No. 60/426,155, filed Nov. 14, 2002.

BACKGROUND

1. Technical Field

The present disclosure relates to electrosurgical instruments and, more particularly, to open or endoscopic electrosurgical instruments having compressible or elastomeric end effector assemblies for use in sealing various tissues.

2. Background

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to affect hemostasis by heating the tissue and blood vessels to coagulate, cauterize and/or seal.

By utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

In order to seal large vessels, two predominant mechanical parameters must be accurately controlled—the pressure applied to the vessel and the gap distance between the electrodes—both of which are affected by the thickness of the sealed vessel to be sealed. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.005 inches. Below this range, the seal may shred or tear and above this range the opposing tissue layers may not be properly or effectively sealed.

With respect to smaller vessels, the pressure applied to the tissue tends to become less relevant whereas the gap distance between the electrically conductive surfaces becomes more significant for effective sealing. With smaller vessels, the chances of the two opposed electrically conductive surfaces of the electrosurgical forceps touching during activation increases as the size of the vessel becomes smaller.

The process of coagulating small vessels is fundamentally different than electrosurgical vessel sealing. For the purposes herein, "coagulation" is defined herein as a process of desiccating tissue wherein the tissue cells are ruptured and dried. "Vessel sealing" meanwhile is defined herein as a process of liquefying the collagen elastin and ground substances in the tissue so that it reforms into a cohesive, fused mass. Coagulation of small vessels is sufficient to permanently close the vessel lumen. Larger vessels need to be sealed to assure permanent closure.

U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the opposing tissue layers which in turn may result in an ineffective or non-uniform seal. For example and with particular respect to variously-sized tissues, many of these references disclose instruments which unevenly compress the tissue across the jaw surface which is not conducive to consistent or effective tissue sealing.

Many of these instruments rely on clamping pressure alone to procure proper sealing thickness and are not designed to take into account gap tolerances and/or parallelism and flatness requirements which are parameters which, if properly controlled, can assure a consistent and effective tissue seal. For example, it is difficult to adequately control thickness of the resulting sealed tissue by controlling clamping pressure alone for either of many reasons: 1) if tissue is initially thin or if too much force is applied, there is a possibility that the two electrically conductive surfaces of the instrument will touch and energy will not be transferred through the tissue resulting in an ineffective seal; 2) if tissue is thick or too low a force is applied, the tissue may pre-maturely move prior to activation and sealing and a thicker, less reliable seal may be created; or 3) if the tissue is thick, over compression may lead to tissue vaporization and a less reliable seal may be created.

Moreover, the performance of certain existing clamping RF delivery systems is limited due to their inherent tendency to arc and short once the directly opposing electrodes have been drawn into close proximity with one another. Maintaining a functional and reliable system with a directly opposed configuration requires tight tolerances on specific parameters such as electrode gap and jaw parallelism.

Thus, a need exists to develop an electrosurgical instrument which effectively and consistently seals variously-sized tissue and solves many of the aforementioned problems known in the art.

SUMMARY

The present disclosure relates to electrosurgical instruments having compressible or elastomeric end effector assemblies for use in sealing various tissues. In accordance with one aspect of the present disclosure, an electrosurgical instrument for sealing vessels includes a housing having a shaft attached thereto and an end effector assembly attached to a distal end of the shaft, wherein the end effector assembly includes first and second jaw members attached thereto. The jaw members are movable relative to one another from a first position for approximating tissue to at least one additional position for grasping tissue therebetween.

Preferably, each of the jaw members includes an elastomeric material disposed on an inner facing tissue contacting surface thereof. Each of the elastomeric materials includes an electrode disposed therein. Preferably, the electrodes are offset a distance X relative to one another such that when the jaw members are closed about the tissue and when the electrodes are activated, electrosurgical energy flows through the tissue in a generally coplanar manner relative to the tissue contacting surfaces. Preferably, the offset distance X is in the range of about 0.005 inches to about 0.0.200 inches. It is envisioned that at least one of the jaw members includes means for regulating the distance X dependent upon tissue thickness or tissue type.

It is envisioned that the elastomeric material is either silicone, polyurethane or other thermoplastic elastomers such as santoprene (or combinations thereof). One or more of the above substances may also be combined to form an alloy with one or more of the following substances: nylon, syndiotactic polystryrene, Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion or Acrylonitrile Styrene Acrylate. Preferably, the compressible material has a comparative tracking index (CTI) value of about 300 to about 600 volts.

It is envisioned that the electrosurgical system include at least one sensor which provides information to a feedback circuit for regulating the electrosurgical energy through the tissue. Preferably, the sensor measures at least one of tissue impedance, tissue temperature, tissue pressure, light transmission, and tissue thickness.

Preferably, at least one of the jaw members includes a plurality of electrodes across the width thereof and the electrosurgical instrument includes means for selecting one of the plurality of electrodes for electrically opposing the electrode disposed on the other of the jaw members. The selecting means includes a sensor which measures at least one of tissue impedance, tissue temperature and tissue thickness.

In one embodiment, the electrodes are wire electrodes which project from the tissue contacting surfaces of the elastomeric material into contact with the tissue. In another embodiment, the elastomeric material on each of the jaw members includes an electrode which is partially disposed therein. It is envisioned that upon grasping of tissue between the jaw members, each of the electrodes deflect inwardly relative to the tissue contacting surfaces in response to the tissue reaction forces.

In yet another embodiment, the electrodes are recessed within the elastomeric material. It is further contemplated that the tissue contacting surface of each electrode is substantially crowned.

In another aspect of the present disclosure, the electrosurgical instrument includes an end effector assembly attached to a distal end of the shaft. The end effector assembly includes first and second jaw members attached thereto. The jaw members are movable relative to one another from a first position for approximating tissue to at least one additional position for grasping tissue therebetween.

In the present embodiment each of the jaw members includes an electrically insulative material (e.g., a material having a high CTI value) disposed on an inner facing tissue contacting surface thereof and an elastomeric material disposed between each jaw member and a respective insulative material. It is envisioned that the elastomeric material may also be made from one or more electrically insulative materials. Each of the insulative materials includes an electrode disposed therein. The electrodes are offset a distance X relative to one another such that when the jaw members are closed about the tissue and when the electrodes are activated, electrosurgical energy flows through the tissue in a generally coplanar manner relative to the tissue contacting surfaces.

It is envisioned that the insulative material on each of the jaw members includes an electrode which is partially disposed therein. It is further envisioned that each of the electrodes are recessed within the insulative material.

Other objects and features of the present disclosure will become apparent from consideration of the following description taken in conjunction with the accompanying drawings.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

DETAILED DESCRIPTION

Preferred embodiments of the presently disclosed electrosurgical instrument are described in detail herein with reference to the drawing figures wherein like reference numerals identify similar or identical elements. In the drawings and in the description which follows, the term "proximal", as is traditional will refer to the end of the electrosurgical instrument which is closest to the operator, while the term "distal" will refer to the end of the instrument which is furthest from the operator.

Figure 1:
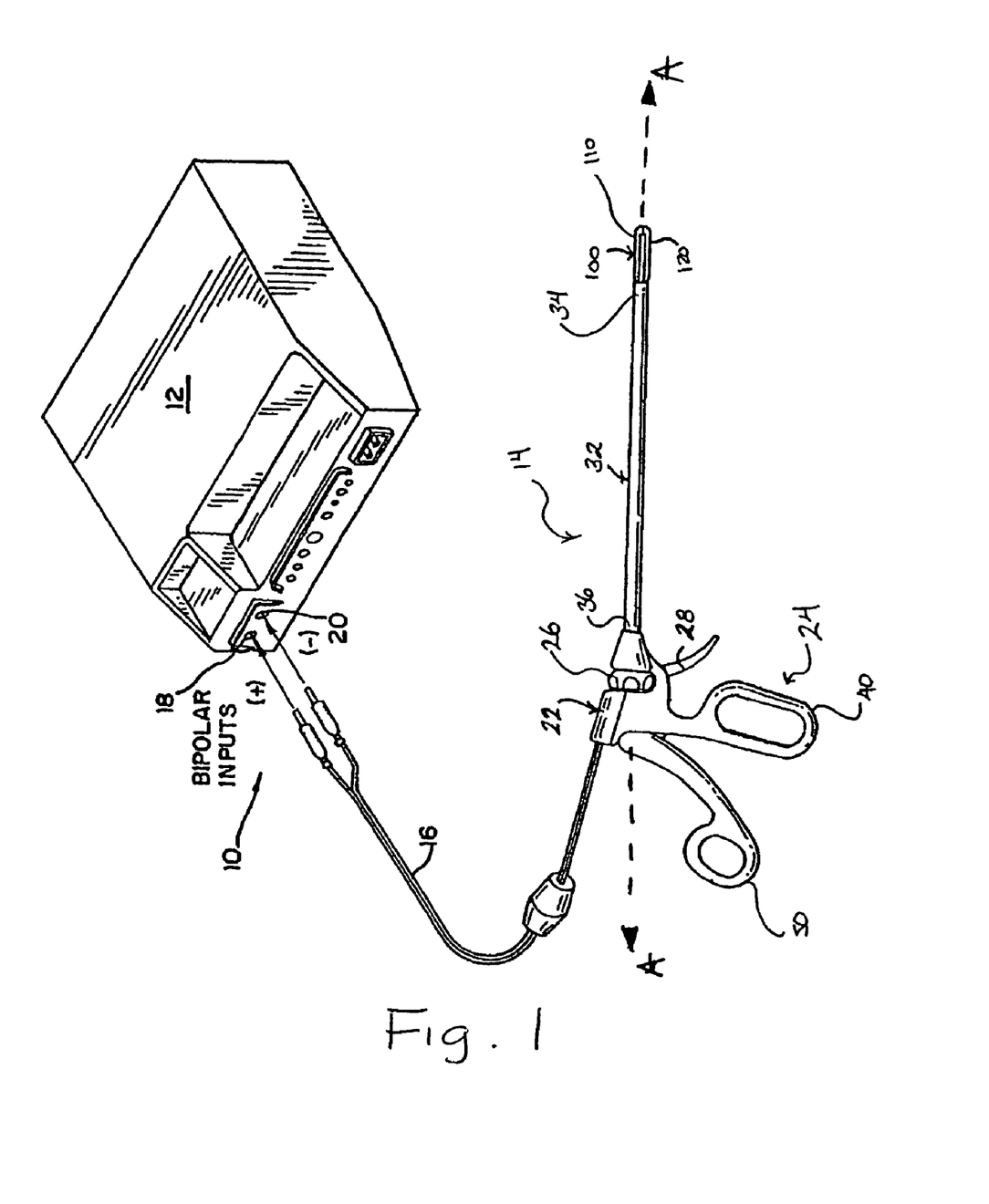
FIG. 1 is a perspective view of an exemplary electrosurgical instrument in accordance with the present disclosure, and associated with an electrosurgical generation.

Referring initially to FIG. 1, there is seen a perspective view of an electrosurgical instrument system in accordance with an exemplary embodiment of the present disclosure, generally indicated as reference numeral 10. Electrosurgical instrument system 10 includes an electrosurgical energy generator 12 and electrosurgical forceps 14. A cable 16 electrically connects forceps 14 to generator 12 via clips 18 and 20.

Forceps 14 include a housing 22, a handle assembly 24, a rotating assembly 26, a trigger assembly 28 and an end effector assembly 100 which mutually cooperate to grasp and divide tubular vessels and vascular tissue. More particularly, forceps 14 include a shaft 32 which has a distal end 34 dimensioned to mechanically engage end effector assembly 100 and a proximal end 36 which mechanically engages housing 22. While the illustrated forceps 14 are intended for use in minimally invasive endoscopic surgical procedures, the principles of the present disclosure are equally applicable to forceps designed for use in open surgical procedures.

Handle assembly 24 includes a fixed handle 40 and a movable handle 50. Fixed handle 40 is integrally associated with housing 22 and movable handle 50 is movable relative to fixed handle 40 as explained in more detail below with respect to the operation of forceps 14. Rotating assembly 26 is preferably attached to a distal end of housing 22 and is rotatable in either direction about a longitudinal axis "A" of shaft 32.

As mentioned above, end effector assembly 100 is attached to distal end 34 of shaft 32 and includes a pair of opposing jaw members 110, 120. Movable handle 50 of handle assembly 24 is ultimately connected to a drive rod (not shown) which, together, mechanically cooperate to impart movement of jaw members 110, 120 from an open position wherein jaw members 110, 120 are disposed in spaced relation relative to one another to a clamped or closed position wherein jaw members 110, 120 cooperate to grasp tissue therebetween.

It is envisioned that forceps 14 may be designed such that it is fully or partially disposable depending upon a particular purpose or to achieve a particular result. For example, end effector assembly 100 may be selectively and releasably engageable with the distal end 34 of shaft 32 and/or the proximal end 36 of shaft 32 may be selectively and/or releasably engageable with housing 22 and handle assembly 24. In either of these two instances, forceps 14 would be considered "partially disposable" or "reposable", i.e., a new or different end effector assembly 100 (or end effector assembly 100 and shaft 32) selectively replaces the old end effector assembly 100 as needed.

An exemplary electrosurgical energy generator 12 is disclosed in U.S. Pat. No. 6,068,627 to Orszulak, et al. and available from Valleylab—a division of Tyco Healthcare, LP as the Ligasure™ vessel sealing generator and includes an identifying circuit (not shown) therein which is responsive to information and which transmits a verification signal to generator 12 and further includes a switch (not shown) connected to the identifying circuit which is responsive to the signaling of the identifying circuit.

Each jaw member 110, 120 is manufactured from a sufficiently rigid material (i.e., stainless steel) which is resistant to deformation as a result of clamping forces acting thereon. Preferably, jaw members 110, 120 are manufactured from an electrically non-conductive material, such as, for example, a polymer, carbon-fiber, a ceramic-like material or a combination thereof (i.e., Teflon polytetreflouroethylene) which is also resistant to deformation forces.

Figure 2:
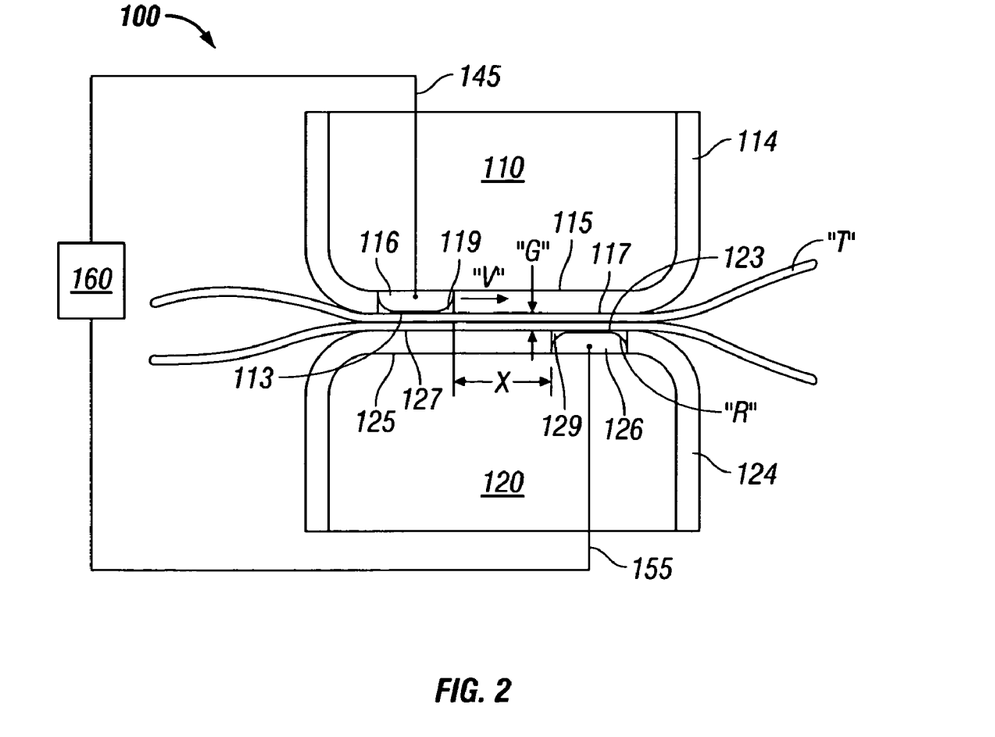
FIG. 2 is a transverse, cross-sectional end view of one embodiment according to the present invention showing a pair of opposing jaw members each having a resilient tissue contact surface with an electrode housed therein.
Figure 3:
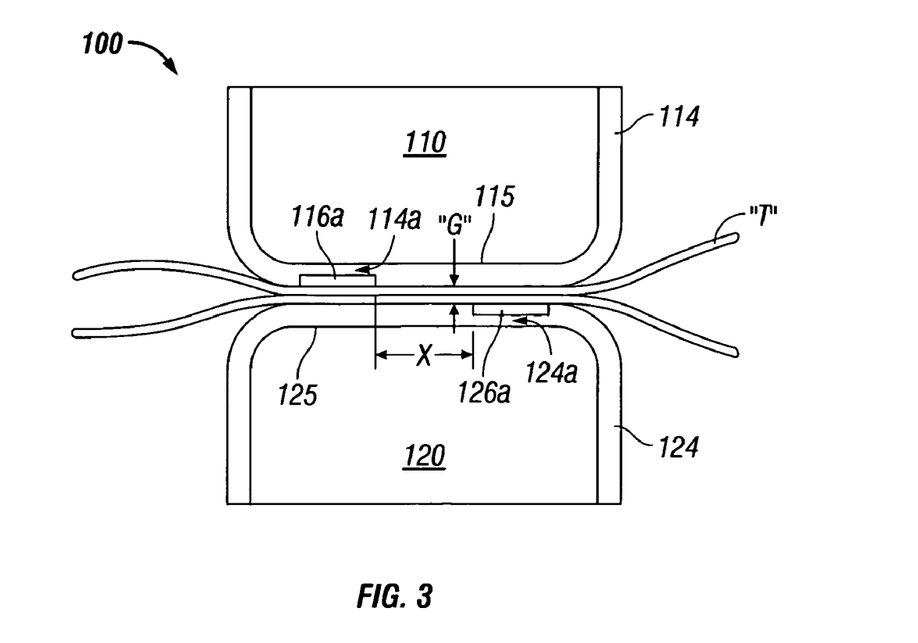
FIG. 3 is a transverse, cross-sectional end view of another embodiment according to the present disclosure wherein the electrodes are partially housed within the resilient tissue contacting surface.
Figure 4:
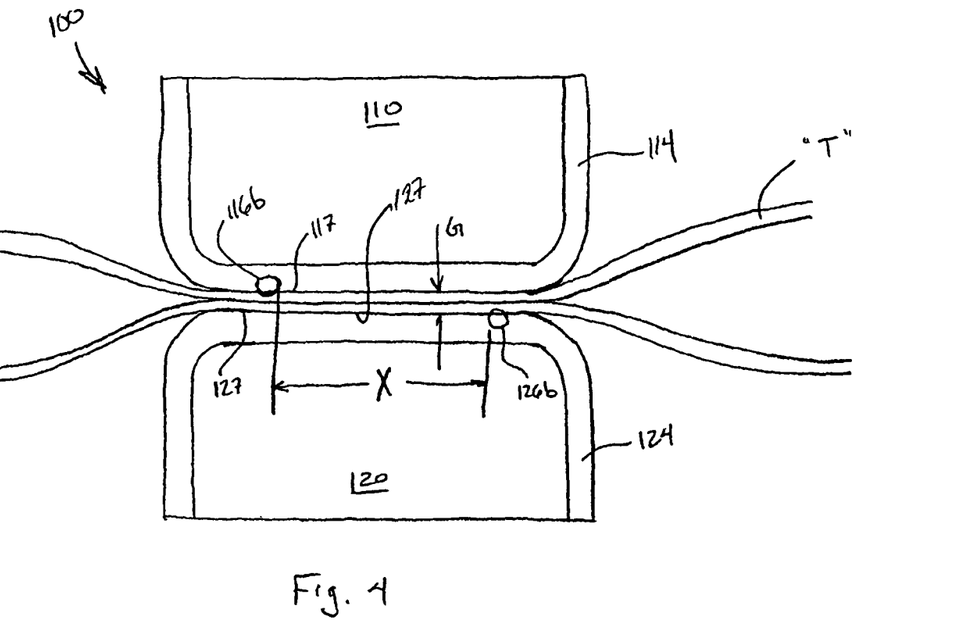
FIG. 4 is a transverse, cross-sectional end view showing a wire electrode disposed in each of the resilient tissue contacting surfaces.
Figure 4A:
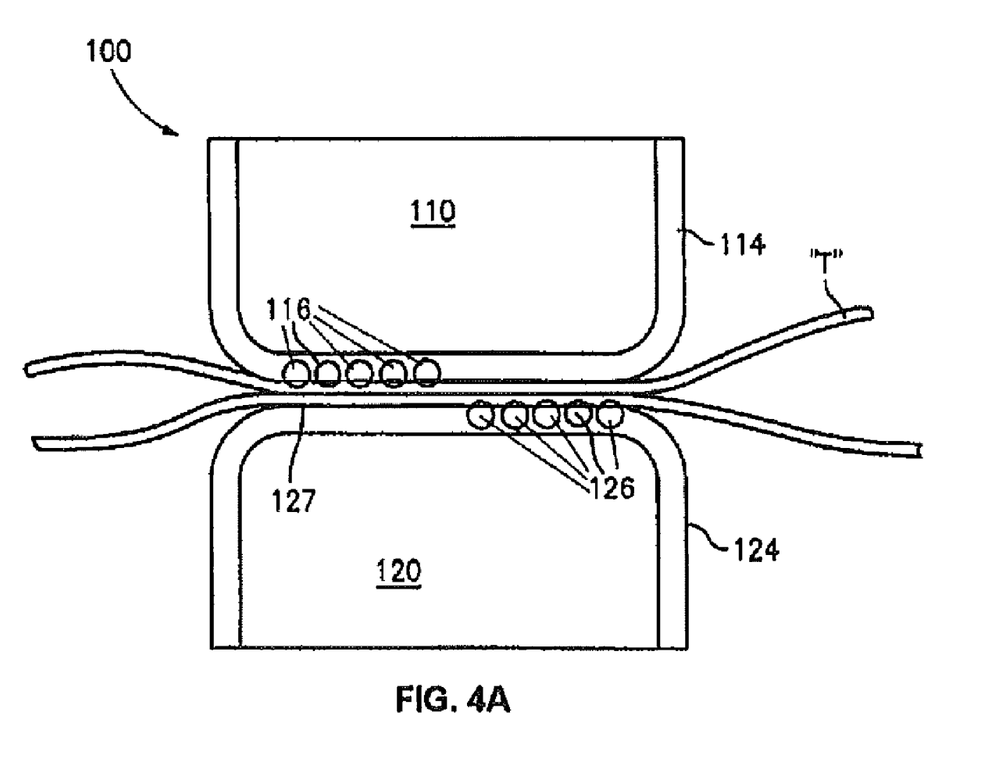
FIG. 4A is a transverse, cross-sectional end view showing a wire electrode array disposed in each of the resilient tissue contacting surfaces in accordance with an embodiment of the present disclosure.

Preferably, each jaw member 110, 120 is at least partially enveloped in an elastomeric material or shell 114, 124, respectively. Elastomeric material is defined herein as a macromolecular material that returns rapidly to approximately the initial dimensions and shape after substantial deformation by a weak stress and release of the stress (strain ~100 to 200%). As seen in FIGS. 2-4, elastomeric shells 114, 124 substantially surround the outer periphery of jaw members 110, 120. Preferably, the elastomeric shells 114, 124, cover the opposing tissue contacting surfaces 115, 125 of jaw members 110, 120, respectively, and are dimensioned to at least partially house an electrode 116, 126 therein.

Preferably, the elastomeric shells 114, 124 are at least partially made from a compressible, electrically non-conductive elastomeric material having a high CTI (Comparative Tracking Index) value of about 300 to about 600 volts in order to reduce surface tracking and possible collateral damage to tissue. It is envisioned that the elastomeric material includes either silicone, polyurethane or another thermoplastic elastomers such as santoprene (or combinations thereof. It is also envisioned that one or more of the above substances may also be combined to form an alloy with one or more of the following substances: nylons and syndiotactic polystryrenes such as QUESTRA® manufactured by DOW Chemical, Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate. Preferably, the elastomeric materials have a low moisture absorption (e.g., less than about 4%) in order to maintain material performance after continual use in fluid rich environments. It has also been discovered that certain coatings can be utilized either alone or in combination with one of the above materials in order to reduce other electrosurgical effects at the tissue contacting site, e.g., flashover.

Each electrode 116, 126 of jaw member 110, 120, respectively, is electrically coupled to generator 12 for delivering bipolar energy across the tissue "T" when grasped. More particularly, electrode 116 is connected to a first electrical potential and electrode 126 is connected to a second electrical potential such that, when energized, electrosurgical energy is transferred through tissue "T" disposed between respective jaw members 110 and 120.

Electrodes 116, 126 are each at least partially disposed within respective elastomeric shells 114, 124 of each jaw member 110, 120 and are preferably disposed on opposite sides of jaw members 110, 120. More particularly, and as best seen in the end views of FIGS. 2-5, electrodes 116, 126 are spaced a transverse distance "X" from one another. Preferably, in accordance with the present disclosure, distance "X" is from about 0.005 inches to about 0.200 inches, a range of about 0.050 inches to about 0.150 inches is preferred to insure proper seal width. Accordingly, when jaw members 110, 120 are in the closed position, electrodes 116, 126 create an electrical path therebetween which is substantially coplanar to opposing tissue engaging surfaces 115 and 125 as will be explained in more detail below.

It is envisioned that the outer surface of electrodes 116, 126 may include a nickel-based material, coating, stamping, and/or metal injection molding which is designed to reduce adhesion between electrodes 116, 126 and the surrounding tissue during activation and sealing. Moreover, it is also contemplated that the tissue contacting surfaces of electrodes 116, 126 may be manufactured from one (or a combination of one or more) of the following materials: nickel-chrome, chromium nitride, MedCoat 2000 manufactured by The Electrolizing Corporation of OHIO, Inconel 600 and tin-nickel. It is further envisioned that tissue contacting surfaces 115, 125 may also be coated with one or more of the above materials to achieve the same result, i.e., a "non-stick surface". For example, Nitride coatings (or one or more of the other above-identified materials) may be deposited as a coating on another base material (metal or nonmetal) using a vapor deposition manufacturing technique. Preferably, the non-stick materials are of a class of materials that provide a smooth surface to prevent mechanical tooth adhesions. As can be appreciated, reducing the amount that the tissue "sticks" during sealing improves the overall efficacy of the instrument.

It is also contemplated that the tissue contacting surfaces 115, 125 of jaw members 110, 120 can include or be coated with these non-stick materials (not shown). When utilized on contacting surfaces 115, 125, these materials provide an optimal surface energy for eliminating sticking due in part to surface texture and susceptibility to surface breakdown due to electrical effects and corrosion in the presence of biologic tissues. It is envisioned that these materials exhibit superior non-stick qualities over stainless steel and should be utilized on forceps 14 in areas where the exposure to pressure and electrosurgical energy may create localized "hot spots" more susceptible to tissue adhesion.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having contact surfaces 115, 125 made from or coated with Ni200, Ni201 (~100% Ni) also showed improved non-stick performance over typical bipolar stainless steel electrodes.

By way of example, chromium nitride may be applied using a physical vapor deposition (PVD) process that applies a thin uniform coating to the entire electrode surface. This coating produces several effects: 1) the coating fills in the microstructures on the metal surface that contribute to mechanical adhesion of tissue to electrodes; 2) the coating is very hard and is a non-reactive material which minimizes oxidation and corrosion; and 3) the coating tends to be more resistive than the base material causing electrode surface heating which further enhances desiccation and seal quality.

The Inconel 600 coating is a so-called "super alloy" which is manufactured by Special Metals, Inc. located in Conroe, Tex. The alloy is primarily used in environments which require resistance to corrosion and heat. The high Nickel content of Inconel makes the material especially resistant to organic corrosion. As can be appreciated, these properties are desirable for bipolar electrosurgical instruments which are naturally exposed to high temperatures, high RF energy and organic matter. Moreover, the resistivity of Inconel is typically higher than the base electrode material which further enhances desiccation and seal quality.

Turning back to FIGS. 2-5, when jaw members 110, 120 are actuated to grasp tissue "T", a gap "G" is defined between opposing surfaces 117, 127 of elastomeric shells 114, 124. In accordance with the present disclosure, the material of elastomeric shells 114, 124 is selected such that when jaw members 110, 120 are closed onto tissue "T", elastomeric shells 114, 124 will compress and deform in order to maintain a substantially uniform gap "G" across the portion of the jaw which is in contact with the tissue. In particular, each elastomeric shells 114, 124 will have a compression or deflection of about 0.001 inches to about 0.015 inches when the clamping force is between about 40 p.s.i. to about 230 p.s.i. (120 p.s.i. nominal) distributed over tissue contacting surfaces 115, 125 of jaw members 110, 120. In addition, it is envisioned that the elastomeric shells 114, 124 of the present disclosure allow for local pressure compensation along the length thereof to allow for sealing across non-homogeneous structures found within the individual tissue or tissue "T" (such as, for example, bronchi and/or vascular structures found in the lung). More particularly, the elastomeric shells 114, 124 compensate for the reaction forces of vessels and tissues so that end effector assembly 100 (i.e., jaw members 110, 120) will not unintentionally damage the tissue "T" (i.e., over-compress the tissue) during the sealing process.

FIG. 2 shows one embodiment according to the present disclosure wherein electrodes 116, 126 are encased in pockets 119, 129, in shells 114 and 124, respectively. Electrodes 116, 126 preferably include an outer edge radius "R" which is designed to reduce negative tissue effects during activation. The electrodes 116, 126 may also be crowned to reduce negative tissue effects during activation. Preferably, the radiused edge "R" includes a radius of about 0.005 inches at the exposed tissue contacting edges. It is envisioned that the radiused edges, in conjunction with placing electrodes 116, 126 within pockets 119, 129 of the elastomeric shells 114, 124 reduces current densities at the inner most corner of electrodes 116, 126. Areas of high current densities may result in the unintentional damage to the tissue during sealing.

It is believed that the distance "X" between adjacent electrodes 116 and 126 plays an important role in sealing vessels. Using computer simulations and histological evidence, it has been demonstrated that a non-uniform power-density exists due to the electrical and thermal properties of tissue. This results in a non-uniform temperature distribution in which temperature is greater in a region centrally located between the electrodes. Impedance in this central region can rise quickly creating an insulative barrier to further current flow across the tissue, resulting in inadequate sealing at the electrode edges. The greater the distance "X" is between the electrodes 116, 126 the greater the effect of the non-uniform temperature distribution. On the other hand if the distance "X" is too small, the resulting seal width may be inadequate to insure effective seal strength. Thus, it has been determined that the distance "X", the distribution of energy across the seal and the relative size of the seal itself are all important parameters which must be properly considered during the sealing process. As a result, it has been found that the preferred distance "X," as described above, is from about 0.005 inches to about 0.200 inches.

It is envisioned that all of these parameters may be monitored and regulated as a part of the disclosures herein. For example, the electrosurgical system may include one or more sensors 145, 155, respectively, which measure tissue temperature, tissue impedance, tissue pressure, light transmission, or tissue thickness prior to, during, or after the sealing process. These parameters can be relayed back to the generator 12 in a feedback loop circuit 160 to predetermine the proper amount of electrosurgical energy required to effectively seal the tissue or monitor and adjust the electrosurgical energy during the overall sealing process. Moreover, it is envisioned that the jaw members 110, 120 may be constructed such that the distance "X" is variable depending upon tissue thickness. This can be accomplished by constructing the electrodes 116, 126 such that at least one is moveable transversely across the sealing surface, as indicated by arrow "V" in FIG. 2, or by having an array of electrodes across the sealing surfaces 115, 125. When utilizing an array of electrodes, each electrode is electrically coupled to the generator 12 to automatically select the appropriate opposing electrode pairs to effect the proper seal across the tissue depending upon the tissue thickness and tissue type.

FIG. 3 shows an alternate embodiment of the present disclosure wherein the electrodes 116a, 126a are partially disposed within the shells 114a, 124a, respectively. It is envisioned that partially disposing the electrodes 116a, 126a within shell 114a, 124a will allow the electrodes 116a, 126a to partially deflect when the jaw members 110 and 120 cooperate to grasp tissue "T". As such, gap "G" is maintained across the portion of the jaw members 110, 120 which are closed about tissue "T". In addition, portions 114*a*, 124*a* act to further insulate electrodes 116*a*, 126*a* from support members 112, 122. Accordingly, support members 112, 122 can be fabricated from electrically conductive materials without interfering (i.e., shorting or arcing) with the electrical fields being transmitted between electrodes 116*a*, 126*a*. It is contemplated that electrodes 116*a*, 126*a* may be radiused in the same manner as electrodes 116, 126 of FIG. 2.

Turning now to FIG. 4, another embodiment of the present disclosure, discloses a pair of opposing wire electrodes 116*b*, 126*b* disposed at least partially within elastomeric shells 114 and 124, respectively, more particularly, electrodes 116*b*, 126*b* are embedded in respective elastomeric shells 114, 124 such that only a portion of electrodes 116*b*, 126*b* are exposed at contacting surfaces 117, 127 of elastomeric shells 114, 124. It is envisioned that wire electrodes 116*b*, 126*b* create the same effect as radiused electrode edges and function to disperse current density. Moreover and similar to the FIG. 3 embodiment depicted above, wire electrodes 116*b*, 126*b* permit a certain degree of deflection at the tissue contacting surfaces 117, 127 which is believed to create a more uniform seal.

Figure 5:
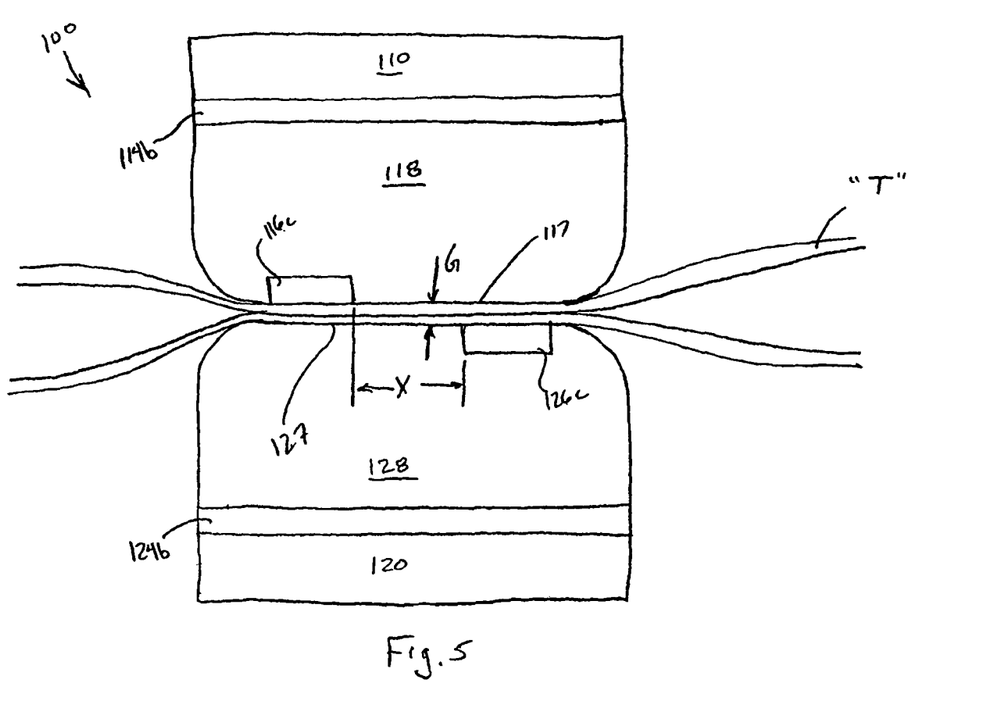
FIG. 5 is a transverse, cross-sectional end view showing a resilient member disposed between the tissue contacting surface and an outer periphery of each of the jaw members.

Turning now to FIG. 5 which shows yet another embodiment of the present disclosure wherein the jaw members 110, 120 each include a layer of elastomeric compressible material 114*b*, 124*b* disposed thereon. More particularly, each jaw member 110, 120 preferably further includes an insulating member 118, 128, respectively, having a respective layer of compressible material 114*b*, 124*b* disposed therebetween. A pair of electrodes 116*c*, 126*c* are disposed in the insulating members 118, 128 and are spaced a distance "X" across the respective contacting surfaces 117, 127. When jaw members 110, 120 close about tissue "T", the insulating members 118, 128 and the electrodes deflect by virtue of the disposition of the compressible material 114*b*, 124*b* between the jaw members 110, 120 and insulating members 118, 128. Electrically insulative spacers may be incorporated on the tissue contacting surface (or surfaces) to control gap "G". As such, a gap "G" is uniformly maintained across the width of jaw members 110, 120 when jaw members 110, 120 are closed about tissue "T".

As can be appreciated and in accordance with the present disclosure, the end effector assembly 100 does not necessarily require a fixed electrode gap (created via a stop member between jaw members—See FIG. 7) or jaw parallelism to reduce the incidents of arcing, shorting and fluid wicking between electrodes 116, 126. In fact, due to the adjacent disposition of the opposing electrodes 116, 126, opposing surfaces 117, 127 of jaw members 110, 120 may contact with each other without causing any incidents of arcing, shorting or fluid wicking.

Moreover, the opposing offset configuration of electrodes 116, 126 according to the present disclosure also tends to minimize collateral electrical fields or current flows which, in turn, reduces unwanted thermal damage to adjacent tissue "T" located outside of the intended sealing area. In other words, the positioning of electrodes 116, 126 on opposite jaw members 110, 120 limits current flow to between the intended sealing area such that stray currents do not extend to tissue outside the lateral boundaries of jaw members 110, 120. Accordingly, enhanced current flow through the tissue is achieved.

Figure 6:
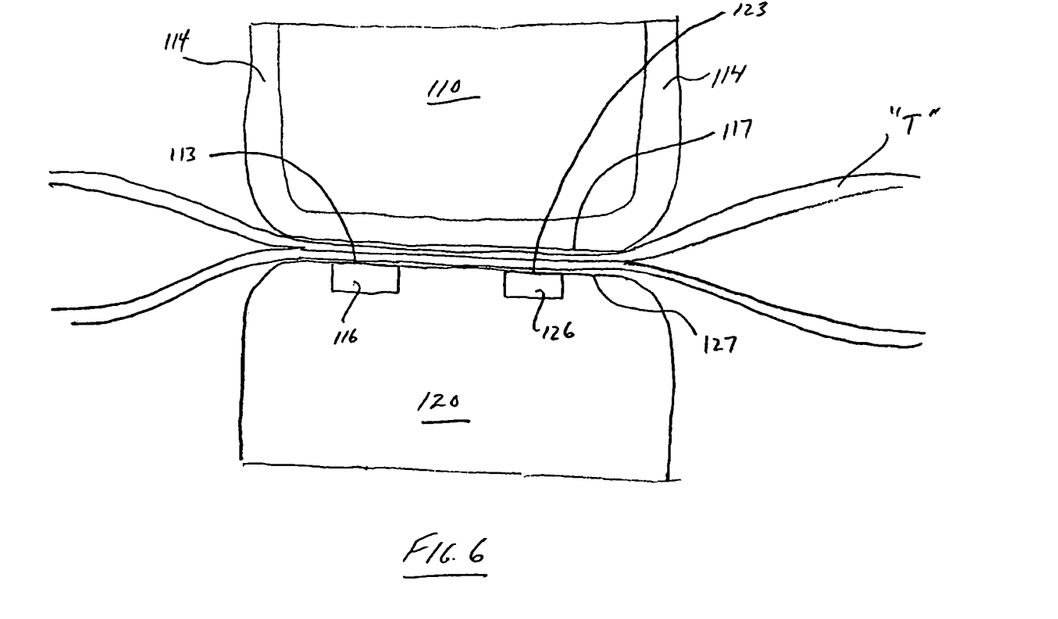
FIG. 6 is a transverse, cross-sectional end view showing an alternate embodiment of the present disclosure wherein the electrodes are disposed on the same jaw member.

FIG. 6 shows an alternate embodiment of the present disclosure wherein the electrode 116, 126 are disposed on the same jaw member, e.g., jaw member 120. The elastomeric material 114 is disposed on the opposite jaw member 110.

Figure 7:
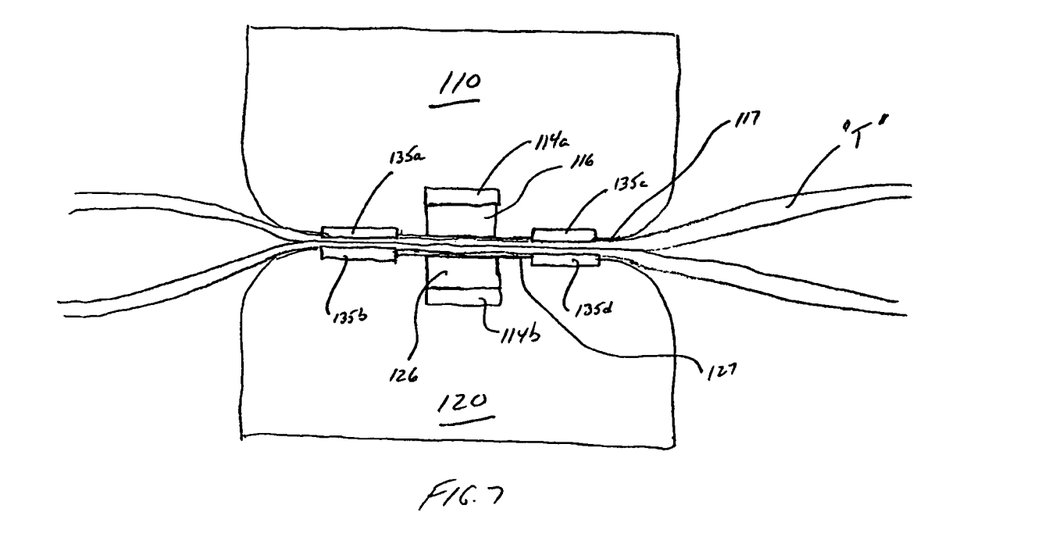
FIG. 7 is a transverse, cross-sectional end view showing another alternate embodiment of the present disclosure wherein the jaw members include a series of stop members for controlling the gap distance between jaw members during sealing.

FIG. 7 shows another embodiment of the present disclosure wherein at least one of the jaw members includes a stop member 135*a* (or series of stop members 135*a*-135*d*) disposed on the tissue contacting surface 117, 127 to regulate the gap distance "G" between opposing jaw members 110 and 120. The electrodes 116 and 126 are diametrically opposed to one another and are supported within each jaw member 110 and 120 by an elastomeric material 114*a*, 114*b*, respectively. It is envisioned that this configuration allows the electrodes 116, 126 to self-align if the alignment between the two electrodes 116, 126 is slightly skewed or non-parallel.

Although the subject apparatus has been described with respect to preferred embodiments, it will be readily apparent to those having ordinary skill in the art to which it appertains that changes and modifications may be made thereto without departing from the spirit or scope of the subject apparatus.

For example, it is envisioned that electrodes 116, 126 and/or electrodes 116, 126 and elastomeric shells 114, 124 may be selectively removable from jaw members 110, 120 (i.e., snap-fit over jaw members 110, 120) depending on the particular purpose. Alternatively, it is envisioned that electrodes 116, 126 can be conductive strips adhered to the elastomeric shells 114, 124.

It is also envisioned that the opposing surfaces 115, 125 of jaws 110, 120 may be crowned in order to effectively stretch the tissue from the centerline of jaws 110, 120 outwardly upon the clamping or closing of jaws 110, 120. By crowning the opposing surfaces 115, 125, the elastomeric shells 114, 124 progressively collapse from the center outwardly towards their respective lateral ends thus substantially squeezing blood and other fluids out of the tissue prior to sealing. It is believed that this facilitates the sealing process by preventing entrapment of air, blood and excess fluids while placing the tissue under tension.

It is contemplated that the relative length of the electrodes 116, 126 may be regulated depending on the size of the tissue being sealed and/or the location and accessibility of the tissue being sealed.

It is further contemplated that opposing surfaces 115, 125 can be provided with gripping or grasping features, e.g., knurling, teeth, ridges, ribs, or the like, (not shown) in order to facilitate grasping of tissue "T" between jaw members 110, 120. It is still further contemplated that the jaw members 110, 120 may be constructed to close in a non-parallel manner about the tissue "T". For example, it is envisioned that the jaw members 110, 120 may be constructed to close in a tip biased, heal biased, or independently floating manner with respect to parallel about tissue "T". It is also envisioned that only one jaw member may include the elastomeric material and the opposite jaw member may be rigid. For example, the elastomeric material 114 may be disposed on the tissue engaging surface of the jaw member 110 and the opposite jaw member 120 may be made from a rigid, non-conductive material. As can be appreciated, either jaw member 110, 120 in this instance could feasibly house the electrodes 116 and 126.

It is further envisioned that the electrically active and insulative components may be designed to minimize thermal masses in order to improve the overall thermal control of end effector assembly 100.

It is also contemplated that the end effector assembly 100 may include a dividing mechanism, such as, for example, a knife blade (not shown), which may be longitudinally reciprocable between the opposing jaws members 110, 120 to effectively and accurately separate the tissue "T" along the tissue seal.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

What is claimed is:

1. A tissue or vessel sealing instrument, comprising:
   a housing having a shaft attached thereto, the shaft defining a longitudinal axis; and
   an end effector assembly attached to a distal end of the shaft, the end effector assembly including first and second jaw members attached thereto made from a substantially rigid material, at least one jaw member being movable relative to the other jaw member from a first position for approximating tissue to at least one additional position for grasping tissue therebetween;
   each of the jaw members including an elastomeric material disposed on an inner facing tissue contacting surface thereof, the elastomeric material of the first jaw member completely surrounding a first electrode associated therewith, each of the electrodes including a planar tissue-contacting surface disposed transverse to the longitudinal axis, the first electrode and the second electrode being offset a distance X relative to one another, wherein the distance X is variable, wherein the distance X is transverse to the longitudinal axis, such that when the jaw members are closed about the tissue and when the electrodes are activated, electrosurgical energy flows through the tissue in a generally coplanar manner relative to tissue contacting surfaces and generally transverse to the longitudinal axis, the elastomeric material being adapted to compress or deflect about 0.001 inches to about 0.015 inches when the force used to close the jaw members is between about 40 psi to about 230 psi; and
   wherein the substantially rigid material of the jaw members resists deformation when the force used to close the jaw members is between about 40 psi to about 230 psi.

2. The tissue or vessel sealing instrument of claim 1, wherein the elastomeric material is selected from the group consisting of at least one of the following materials: silicone, polyurethane, santoprene, nylon, syndiotactic polystryrene, Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

3. The tissue or vessel sealing instrument of claim 1, wherein the offset distance X is in the range of about 0.005 inches to about 0.200 inches.

4. The tissue or vessel sealing instrument of claim 3, wherein the offset distance X is configured to result in a substantially uniform temperature distribution between the electrodes after activation of the electrodes.

5. The tissue or vessel sealing instrument of claim 1, further comprising at least one sensor which provides information to a feedback circuit for regulating the electrosurgical energy through the tissue.

6. The tissue or vessel sealing instrument of claim 5, wherein the sensor measures at least one of tissue impedance, tissue temperature and tissue thickness.

7. The electrosurgical instrument of claim 1, wherein at least one of the jaw members includes means for regulating the distance X dependent upon tissue thickness or tissue type.

8. The tissue or vessel sealing instrument of claim 1, wherein at least one of the jaw members includes at least one electrode across the width thereof and the electrosurgical instrument includes means for selecting one of the electrodes for electrically opposing the electrode disposed on the other of the jaw members, wherein the means includes a sensor which measures at least one of tissue impedance, tissue temperature and tissue thickness.

9. The tissue or vessel sealing instrument of claim 1, wherein the elastomeric material has a comparative tracking index value of about 300 to about 600 volts.

10. The electrosurgical instrument of claim 1, wherein the electrodes are wire electrodes which project from the tissue contacting surfaces of the elastomeric material into contact with the tissue.

11. The electrosurgical instrument of claim 1, wherein the elastomeric material on each of the jaw members includes an electrode which is partially disposed therein.

12. The electrosurgical instrument of claim 11, wherein upon grasping of tissue between the jaw members, each of the electrodes deflect inwardly relative to the tissue contacting surfaces.

13. The electrosurgical instrument of claim 12, wherein the electrodes are recessed within the elastomeric material.

14. The electrosurgical instrument of claim 13, wherein the tissue contacting surface of each electrode is substantially crowned.

15. The tissue or vessel sealing instrument of claim 1, wherein the temperature along the tissue contacting surfaces of the jaw members is substantially uniform after the electrodes are activated.

16. The tissue or vessel sealing instrument of claim 1, wherein the first electrode is encased within a first pocket, wherein the second electrode is encased within a second pocket, wherein the first pocket is disposed within the elastomeric material of the first jaw member, and wherein the second pocket is disposed within the elastomeric material of the second jaw member.

17. A tissue or vessel sealing instrument, comprising:
    a housing having a shaft attached thereto, the shaft defining a longitudinal axis; and
    an end effector assembly attached to a distal end of the shaft, the end effector assembly including first and second jaw members attached thereto made from a substantially rigid material, at least one jaw member being movable relative to the other jaw member from a first position for approximating tissue to at least one additional position for grasping tissue therebetween;
    each of the jaw members including an elastomeric material disposed on an inner facing tissue contacting surface thereof, the electrodes being offset a distance X relative to one another such that when the jaw members are closed about the tissue and when the electrodes are activated, wherein the distance X is variable, electrosurgical energy flows through the tissue in a generally coplanar manner relative to the tissue contacting surfaces and transversely perpendicular to the longitudinal axis, wherein the elastomeric material is selected from the group consisting of at least one of the following materials; silicone, polyurethane, santoprene, nylon, syndiotactic polystyrene, Polybutylene Terephthalate (PBT), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate, the elastomeric material being adapted to compress or deflect about 0.001 inches to about 0.015 inches when the force used to close the jaw members is between about 40 psi to about 230 psi; and wherein the substantially rigid material of the jaw members resists deformation when the force used to close the jaw members is between about 40 psi to about 230 psi.

18. A tissue or vessel sealing instrument, comprising:

a housing having a shaft attached thereto; and an end effector assembly attached to a distal end of the shaft, the end effector assembly including first and second jaw members attached thereto made from a substantially rigid material, at least one jaw member being movable relative to the other jaw member from a first position for approximating tissue to at least one additional position for grasping tissue therebetween;

each of the jaw members including an elastomeric material disposed on an inner facing tissue contacting surface thereof, the elastomeric material being adapted to compress or deflect about 0.001 inches to about 0.015 inches when the force used to close the jaw members is between about 40 psi to about 230 psi, each of the elastomeric materials including a pocket disposed therein, and each pocket including an electrode disposed therein, the electrodes being offset a distance X relative to one another such that when the jaw members are closed about the tissue and when the electrodes are activated, electrosurgical energy flows through the tissue in a generally coplanar manner relative to the tissue contacting surfaces, wherein the offset distance X is in the range of about 0.005 inches to about 0.200 inches, wherein the distance X is variable, wherein the offset distance X is configured to result in a substantially uniform temperature distribution between the electrodes after activation of the electrodes; and wherein the substantially rigid material of the jaw members resists deformation when the force used to close the jaw members is between about 40 psi to about 230 psi.

19. A tissue or vessel sealing instrument, comprising:

a housing having a shaft attached thereto, the shaft defining a longitudinal axis; and an end effector assembly attached to a distal end of the shaft, the end effector assembly including first and second jaw members attached thereto made from a substantially rigid material, at least one jaw member being movable relative to the other jaw member from a first position for approximating tissue to at least one additional position for grasping tissue therebetween;

each of the jaw members including an elastomeric material disposed on an inner facing tissue contacting surface thereof, the electrodes being substantially longitudinally aligned and being offset a distance X relative to one another such that when the jaw members are closed about the tissue and when the electrodes are activated, electrosurgical energy flows through the tissue in a generally coplanar manner relative to the tissue contacting surfaces, the distance X being variable depending on the thickness of the tissue between the jaw members, the elastomeric material being adapted to compress or deflect about 0.001 inches to about 0.015 inches when the force used to close the jaw members is between about 40 psi to about 230 psi; and wherein the substantially rigid material of the jaw members resists deformation when the force used to close the jaw members is between about 40 psi to about 230 psi.

* * * * *